(12) United States Patent
Jolly (10) Patent No.: US 7,706,888 B2
(45) Date of Patent: Apr. 27, 2010

(54) BI-PLANAR ELECTRODE WITH SHUNTING GATES

(75) Inventor: Claude Jolly, Voels (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 321 days.

(21) Appl. No.: 11/487,162

(22) Filed: Jul. 14, 2006

(65) Prior Publication Data

US 2008/0015669 A1    Jan. 17, 2008

(51) Int. Cl.
*A61N 1/05* (2006.01)
(52) U.S. Cl. ...................................... 607/57
(58) Field of Classification Search ............... 607/2, 607/57
See application file for complete search history.

(56) References Cited

U.S. PATENT DOCUMENTS

| | | | | |
|---|---|---|---|---|
| 4,837,049 A * | 6/1989 | Byers et al. | ............... | 216/6 |
| 5,000,194 A | 3/1991 | Van Den Honert et al. | .. | 128/784 |
| 5,037,497 A * | 8/1991 | Stypulkowski | ............... | 156/245 |
| 5,123,422 A | 6/1992 | Charvin et al | ............... | 128/784 |
| 5,649,970 A | 7/1997 | Loeb et al. | ............... | 607/57 |
| 6,374,143 B1 | 4/2002 | Berrang et al. | ............... | 607/137 |
| 6,493,590 B1 * | 12/2002 | Wessman et al. | ............... | 607/116 |
| 7,047,082 B1 * | 5/2006 | Schrom et al. | ............... | 607/116 |
| 7,051,419 B2 * | 5/2006 | Schrom et al. | ............... | 29/594 |
| 7,107,104 B2 * | 9/2006 | Keravel et al. | ............... | 607/116 |
| 7,146,222 B2 * | 12/2006 | Boling | ............... | 607/116 |
| 7,214,189 B2 * | 5/2007 | Zdeblick | ............... | 600/300 |
| 7,369,901 B1 * | 5/2008 | Morgan et al. | ............... | 607/127 |
| 2003/0097121 A1 | 5/2003 | Jolly et al. | ............... | 604/891.1 |
| 2004/0059392 A1 * | 3/2004 | Parramon et al. | ............... | 607/36 |
| 2005/0222659 A1 * | 10/2005 | Olsen et al. | ............... | 607/116 |
| 2006/0247748 A1 * | 11/2006 | Wahlstrand et al. | ............ | 607/116 |
| 2007/0027514 A1 * | 2/2007 | Gerber | ............... | 607/116 |
| 2007/0027515 A1 * | 2/2007 | Gerber | ............... | 607/116 |
| 2008/0009927 A1 * | 1/2008 | Vilims | ............... | 607/115 |
| 2008/0071313 A1 * | 3/2008 | Stevenson et al. | ............... | 607/2 |

FOREIGN PATENT DOCUMENTS

WO      WO 97/30670 A      8/1997

OTHER PUBLICATIONS

Black, R.C., et al., "Differential Electrical Excitation of the Auditory Nerves," *J. Acoust. Soc. Am.*, Mar. 1980, vol. 67, No. 3, Abstract.

(Continued)

*Primary Examiner*—George Manuel
*Assistant Examiner*—Christopher A Flory
(74) *Attorney, Agent, or Firm*—Sunstein Kann Murphy & Timbers LLP (57) ABSTRACT

A neural stimulator includes an electrically non-conductive carrier and at least two electrically conductive electrodes disposed on opposite sides of the carrier. The electrodes on the opposite sides of the carrier are not electrically connected together. Instead, a signal source is connected to one of the electrodes on one side of the carrier and a return path to the signal source is connected to a corresponding electrode on the other side of the carrier. The corresponding electrode can, but need not be, directly opposite the electrode on the other side of the carrier. The electrodes can be rings, disks, other shapes or combinations thereof. Optionally, the carrier includes low-impedance shunts therethrough.

32 Claims, 10 Drawing Sheets

OTHER PUBLICATIONS

Hanekom, T., Modelling of the Electrode-Auditory Nerve Fibre Interface in Cochlear Prostheses, *Dept. of Electrical, Electronic and Computer Engineering*, Jun. 2001, Chapter 5, Abstract, pp. 111-135.

Holsheimer, J., et al., "Electrical Neuromodulation in Chronic, Intractable Pain," *International ifess*, pp. 1-5, http://www.ifess.org/Services/Consumer_Ed/Pain_Modulation .pdf.

Jolly, C.N., et al., "Guinea Pig Auditory Nerve Response Triggered by a High Density Electrode Array," *Med. Prog. Technol.*, 1997, vol. 21, Suppl. Abstract.

Jolly, C.N., et al., "Quadrupolar Stimulation for Cochlear Prostheses: Modeling and Experimental Data." *IEEE Trans Biomed Eng.* Aug. 1996, 43(8), Abstract.

Deurlo, K.E., et al., "Traverse Tripolar Stimulation of Peripheral Nerve: A Modelling Study of Spatial Selectivity,"*Med. Biol Eng. Comput.*, Jan. 1998, 36(1), Abstract.

Malmivuo, J., et al., "Bioelectromagnetism," 1995, Chapter 22.

Pau, H.W., et al., "An 'Endosteal Eelctrode' for Cochlear Implantation in Cases With Residual Hearing? Feasibility Study: Preliminary Temporal Bone Experiments," *Otol Neurotol*, May 2005, 26(3) Abstract.

Spelman, F.A., et al., "Effects of Electrical Current Configuration on Potential Fields in the Electricity Stimulated Cochlea: Field Models and Measurements," *Ann Otol. Rhinol Laryngol. Suppl.*, Sep. 1995, vol. 166, Abstract.

Spelman, F.A., et al., "Tissue Impedance and Current Flow in the Implanted Ear. Implications for the Cochlear Prosthesis," *Ann. Otol. Rinol. Laryngol. Suppl.*, Sep.-Oct. 1982, vol. 98, Abstract.

Spelman, F.A., et al., "Design of the Cochlear Prosthesis: Effects of the Flow of Current in the Implanted Ear," *Ann Otol. Rhinol. Laryngol. Suppl.*, Mar.-Apr. 1980 vol. 89, Abstract.

Stieglitz, T., "Implantable Microsystems for Monitoring and Neural Rehabilitation, Part II," *Medical Device Technology*, Jan./Feb. 2002.

Rubinstein, J., "How Cochlear Implants Encode Speech," *Current Opinion in Otolaryngology & Head and Neck Surgery*, 2004, vol. 12, pp. 444-448.

Hanekom, T., "Modelling of the Electrode-Auditory Nerve Fibre Interface in Cochlear Protheses," *UPeTD*, Title Page for ETD—09052001-132021; Sep. 2001; http://upetd.up.ac.za/thesis/available/etd-09052001-132021/ (1 of 3)Jul. 6, 2007 12:52:46 PM.

PCT/US2007/073124 International Search Report/Written Opinion dated Nov. 16, 2007.

\* cited by examiner (PRIOR ART)
FIG. 1

(Bottom)

BI-PLANAR ELECTRODE WITH SHUNTING GATES

TECHNICAL FIELD

The present invention relates to electrodes for neural stimulation and, more particularly, to such electrodes disposed on opposite sides of a carrier.

BACKGROUND ART

Electrical stimulation of neural tissue is used for several purposes, including pain control, diagnosis and neural rehabilitation. For example, a cochlear implant (CI) is a small electronic device, part of which is placed under the skin, behind the ear, of a profoundly deaf or severely hard of hearing person. The cochlear implant receives signals from a microphone and electrically stimulates auditory nerves of the wearer. Although hearing through a CI may be different than normal hearing, the wearer perceives sounds and another person can orally communicate with the wearer.

CI and other neural stimulation is accomplished by placing at least one electrode near neural tissue and sending an electrical signal to the electrode. The electrical signal is produced with reference to a second (ground) electrode. That is, the signal is delivered across the two electrodes. The second electrode may be placed near the neural tissue or some distance from the neural tissue. The neural tissue is typically stimulated with a bi-phasic pulse, i.e., first a positive pulse is sent to the electrode, followed almost immediately thereafter by a negative pulse.

Better results are obtained from better focused electrical stimulation. Neural tissues are typically very small. To achieve desired results, selected individual nerves should be stimulated. However, prior art neural stimulation apparatus is unable to deliver well-focused electrical stimulation to neural tissue.

A conventional longitudinal bipolar neural stimulation scheme includes two conducting electrodes arranged side-by-side on an insulated carrier. A signal is fed to a first of the two electrodes, and the other electrode acts as a ground. During the positive phase of the stimulation signal, current flows from one of the electrodes, through the stimulated tissue, into the other (ground) electrode. During the negative phase of the stimulation signal, the current flows in the opposite direction, i.e., out of the ground electrode, through the stimulated tissue, and into the first electrode. Consequently, each of the electrodes acts as a stimulation point, and the stimulation is not well focused.

A conventional longitudinal tripolar scheme includes two ground electrodes flanking a center electrode. In this case, the amount of current that flows through each of the two flanking electrodes is one-half the amount of current that flows through the center electrode. Tripolar schemes produce reasonably well focused stimulation, however they require three electrodes.

SUMMARY OF THE INVENTION

An embodiment of the present invention provides a neural stimulator that includes a nonconductive carrier. The carrier has a first side and a second side substantially opposite the first side. At least one first electrode is disposed on the first side of the carrier, and at least one second electrode disposed on the second side of the carrier. The at least one first electrode is not electrically connected to the at least one second electrode.

The carrier may have a circular, oval, rectangular or other cross-sectional shape.

Each of the at least one first electrode may correspond to one of the at least one second electrode. In this case, each of the at least one second electrode may be centered on a line that perpendicularly bisects the corresponding first electrode. Alternatively, each of the at least one second electrode may be not centered on a line that perpendicularly bisects the corresponding first electrode The neural stimulator may also include a signal source connected to one of the at least one first electrode and to the corresponding second electrode.

The carrier may include at least one shunt gate therethrough. In this case, each shunt gate defines a low-impedance electrical path through the carrier. Some or all of the at least one shunt gate may define a bore through the carrier. Optionally or alternatively, some or all of the at least one shunt gate may include an electrically conductive material.

Some or all of the second electrode may include a ring electrode. Some or all of the ring electrode may be formed by a photolithographic process. Optionally or alternatively, some or all of the ring electrode may be formed by a electrodeposition process. Optionally or alternatively, some or all of the ring electrode may be formed by a laser ablation deposition process.

The at least one first electrode may include a plurality of electrodes arranged in an array. In this case, the at least one second electrode may include a plurality of electrodes, each of the plurality of electrodes including a ring electrode.

The carrier may include at least one shunt gate proximate each first electrode. In this case, each shunt gate defines a low-impedance electrical path through the carrier.

Optionally, each of the at least one first electrode includes at least one ear disposed below a surface of the carrier.

Optionally, the at least one first electrode includes a plurality of first electrodes in a region of the first side of the carrier. The region includes space between the plurality of first electrodes. The at least one second electrode includes an electrically conductive surface on the second side of the carrier. The surface has an area at least as large as the region on the first side of the carrier.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

In accordance with the present invention, methods and apparatus are disclosed for electrically stimulating neural tissue with focused stimulation signals. In one embodiment, one or more pairs of electrodes are disposed on an insulated carrier, such that one of each pair of the electrodes is disposed on one side of the carrier, and the other of the pair of electrodes is disposed on an opposite side of the carrier. An electrical stimulation signal is delivered across the pair of electrodes. Other embodiments, alternatives and options are described below, following a brief discussion of the prior art.

Figure 1:
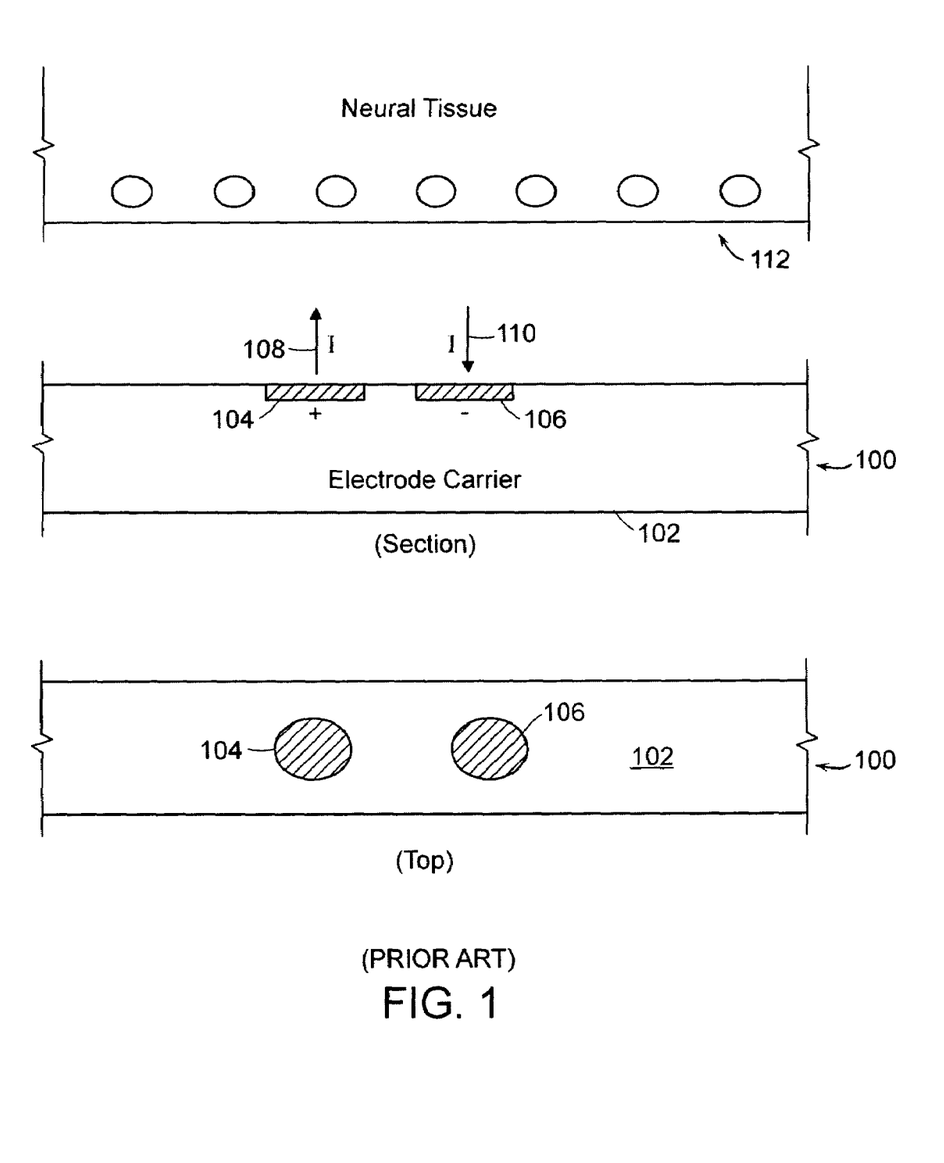
FIG. 1 is cross-sectional and top view of a neural stimulator, according to the prior art.

FIG. 1 is a section and top view of a conventional longitudinal bipolar neural stimulator 100. The stimulator 100 includes an electrically nonconductive carrier 102 and two electrically conductive electrodes 104 and 106 disposed on the carrier 102. The electrodes 104 and 106 are fed, via conductive leads (not shown), by a signal source (not shown). For example, during one phase of biphasic stimulation, one of the electrodes 104 may be fed with a positive pulse (as indicated by the plus sign), and the other electrode 106 may form a return path (as indicated by the minus sign) for the stimulation signal.

Arrows 108 and 110 indicate the general direction of current (I) flow. During another phase, the current flows are reversed. Consequently, neural tissue 112 is stimulated from two locations, namely electrodes 104 and 106, and the stimulation is not well focused. The amount of current (I) flowing through one of the electrodes 104 into or out of tissue adjacent the electrode 104 is equal to the amount of current (I) flowing through the other electrode 106 out of or into tissue adjacent the other electrode 106. In other words, equal currents flow through the two electrodes 104 and 106.

Figure 2:
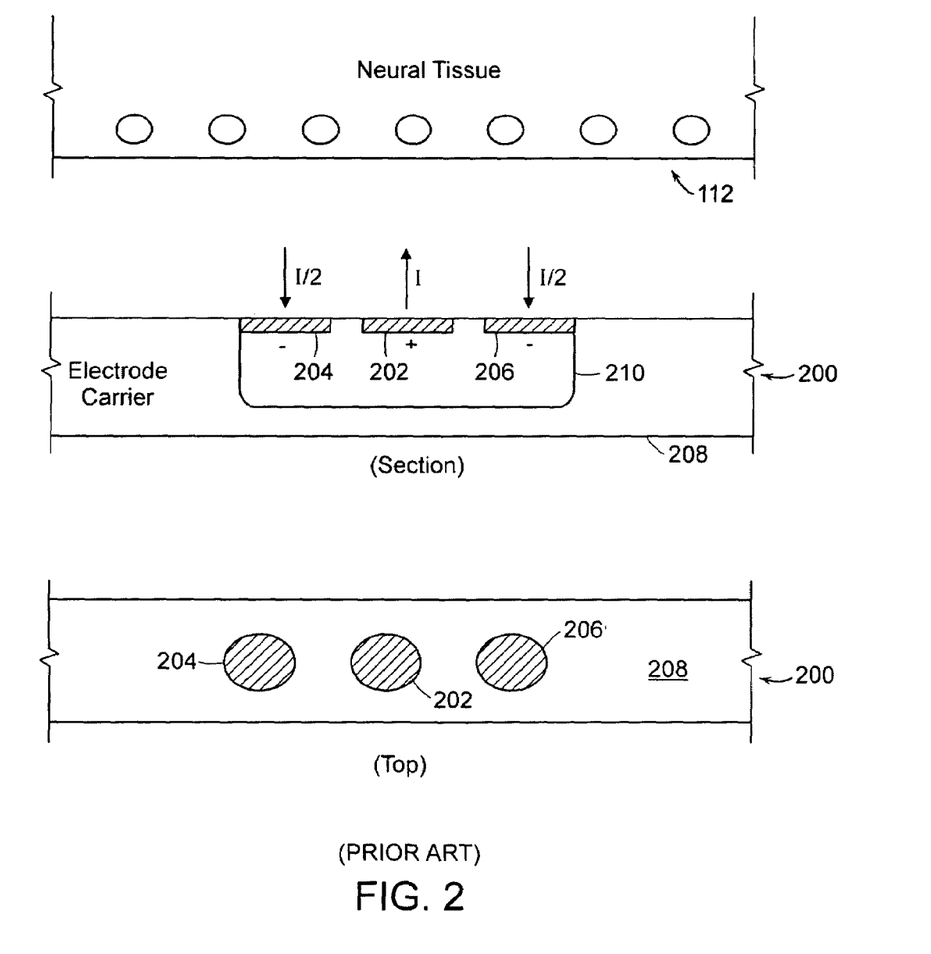
FIG. 2 is cross-sectional and top view of another neural stimulator, according to the prior art.

FIG. 2 is a section and top view of a conventional longitudinal tripolar neural stimulator 200. The stimulator 200 includes three electrodes 202, 204 and 206 on a nonconductive carrier 208. Two of the electrodes 204 and 206 are electrically connected together, such as by a lead 210. The current that flows through the center electrode 202 is designated I. One-half of this current (i.e., I/2) flows through each of the two outer electrodes 204 and 206. Again, the stimulation is not well focused.

Figure 3:
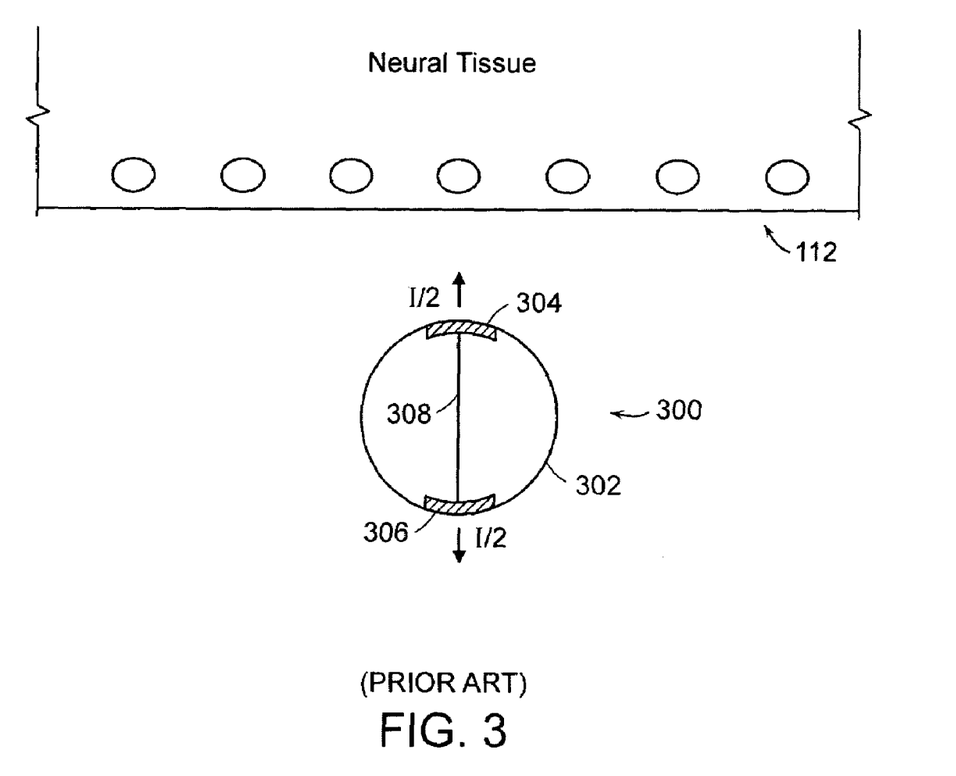
FIG. 3 is cross-sectional and top view of yet another neural stimulator, according to the prior art.

FIG. 3 is a section view of yet another conventional neural stimulator 300. The stimulator 300 includes a nonconductive carrier 302 and two electrodes 304 and 306. The two electrodes 304 and 306 are electrically connected together, such as by a lead 308. Consequently, half the stimulation current (I/2) flows through each of the two electrodes 304 and 306.

The stimulation signal is provided with reference to a distant ground electrode (not shown). As with the other prior-art neural stimulators, the stimulation is not well focused.

Virtual Quadtrupolar Neural Stimulator

Figure 4:
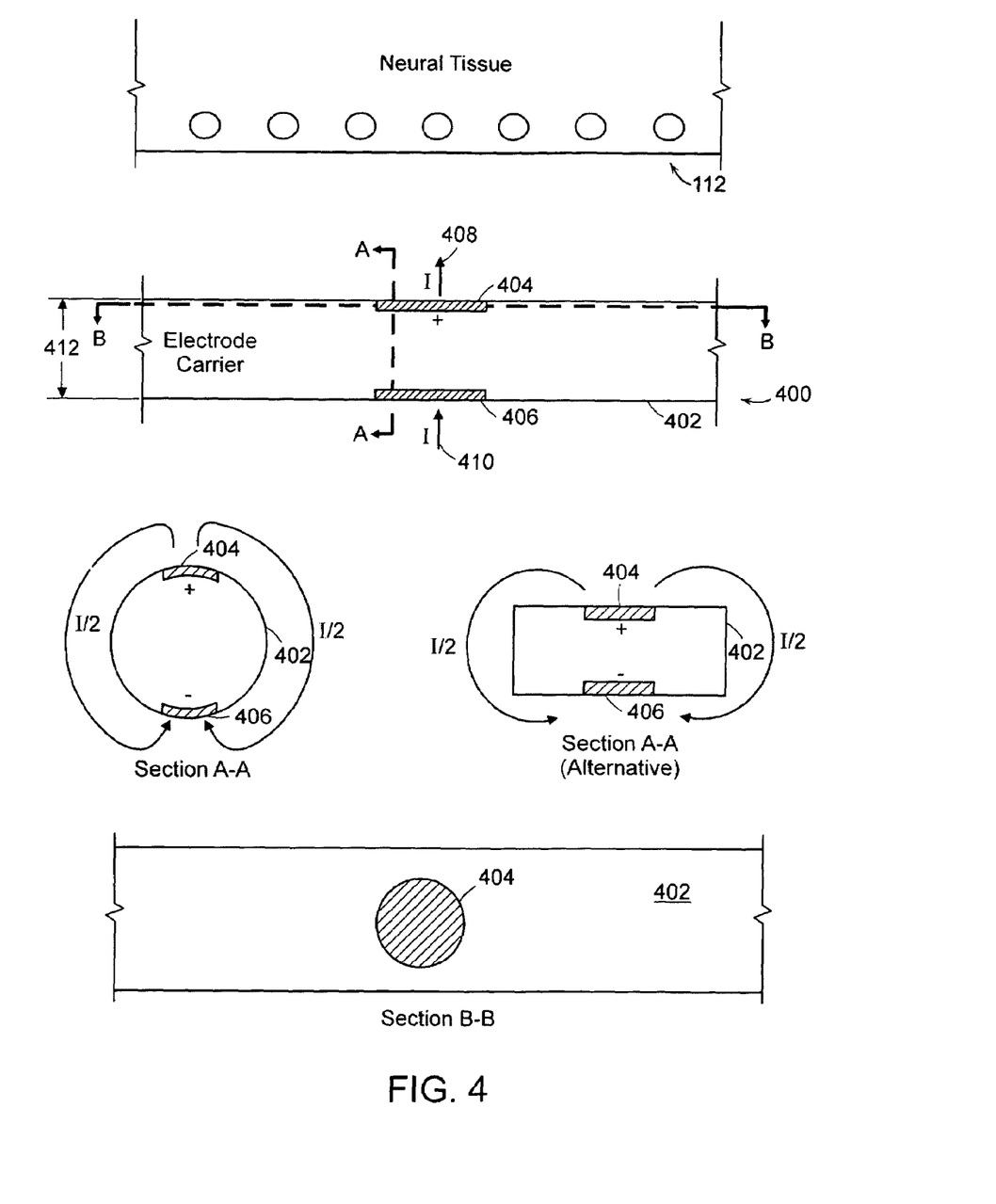
FIG. 4 is cross-sectional and top view of a neural stimulator, according to one embodiment of the present invention.

FIG. 4 is a section view of a neural stimulator 400, according to one embodiment of the present invention. The stimulator 400 includes a nonconductive carrier 402 and two conductive electrodes 404 and 406 disposed on opposite sides of the carrier 402. However, unlike the prior art, the two electrodes 404 and 406 are not electrically connected together. Instead, the stimulating signal is provided (via leads, not shown) to one of the electrodes 404 with respect to the other electrode 406. That is, the signal is provided across the electrodes 404 and 406. Thus, the same amount of current (I) flows through each of the electrodes 404 and 406. Arrows 408 and 410 indicate current flow during a portion of the stimulation signal. During another portion of the stimulation signal the current flow may be reversed.

As shown in Section A-A, the carrier 402 can be round or oval in cross-sectional shape. Alternatively, as shown in Section A-A (Alternative), the carrier 402 can be rectangular in cross-sectional shape. In other embodiments (not shown), the carrier 402 can have other cross-sectional shapes. The thickness 412 of the carrier 402, i.e., the distance between the two electrodes 404 and 406, along with the cross-sectional shape of the carrier 402 can be selected to provide a stimulation field having desired characteristics. For example, a larger distance between the electrodes 404 and 406 requires a less powerful stimulation signal than a smaller separation distance; however, a larger separation often yields a less focused stimulation field.

As shown by the arrows in Section A-A and Section A-A (Alternative), one-half the current (i.e., I/2) flows on each side of the carrier 402. Consequently, the neural tissue 112 is stimulated from a single point, i.e., the electrode 404 facing the neural tissue 112. Typically, the stimulator 400 is positioned such that it is in a plane parallel to a plane of the neural tissue 112. Thus, the stimulating electrode 404 is in the parallel plane. The other electrode 406 is also in a plane parallel to the neural tissue 112, but the other electrode's 406 plane is located on the opposite side of the stimulating electrode 404. The plane of the other electrode 406 is referred to herein as "antineural," i.e., on the opposite side from the plane of the stimulating electrode 404. I have discovered that disposing the return electrode 406 antineural focuses the stimulating signal.

As viewed from the neural tissue 112, and as seen in section B-B, the neural stimulator 400 can have any shape, such as round or rectangular.

The electrodes 404 and 406 and leads (not shown) can be fabricated using conventional photolithographic, electrodeposition, pulsed laser ablation deposition or other techniques. For example, platinum can be deposited on a conventional carrier.

Shunt Gates

Figure 5:
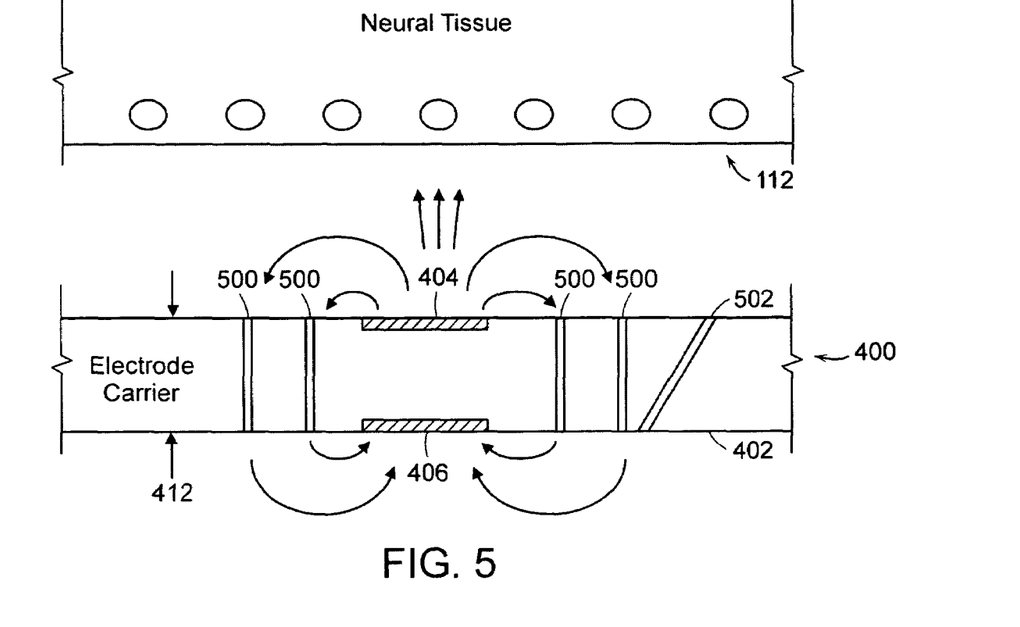
FIG. 5 is cross-sectional view of a neural stimulator, according to another embodiment of the present invention.
Figure 6:
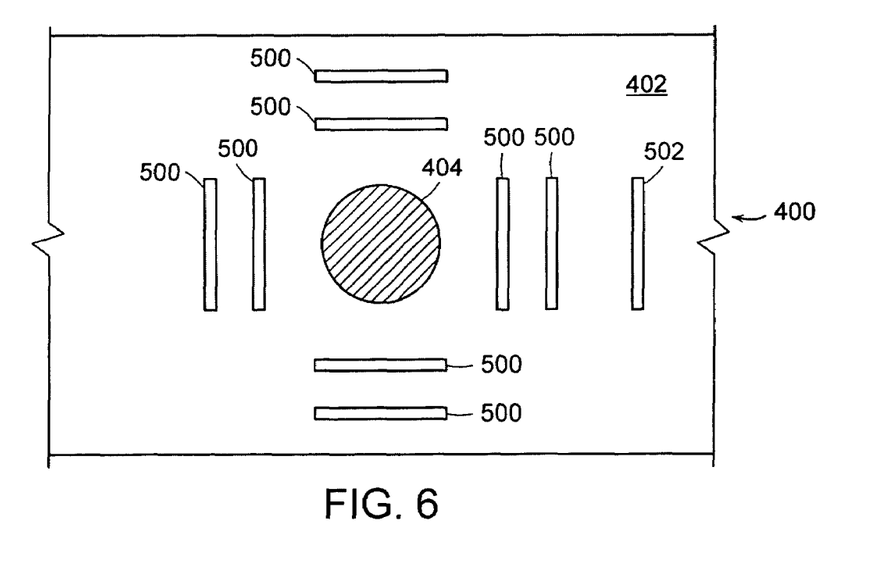
FIG. 6 is a top view of the neural stimulator of FIG. 5.

Optionally, as shown in FIGS. 5 and 6, "shunt gates" 500 are included in the carrier 402 of the neural stimulator 400. (FIG. 6 is a top view of the neural stimulator 400.) The shunt gates 500 provide conductive or low-impedance paths through the carrier 402 for at least some of the stimulation signal. Thus, at least some of the current from the electrode 404 flows through the shunt gates 500 to the other electrode 406, rather than flowing all the way around the carrier 402. I have discovered that, in some circumstances, the shunt gates 500 provide improved focus of the stimulation signal.

The shunt gates 500 can be open passages, holes, grooves, slots or other openings (collectively herein referred to as "bores") formed through or on the carrier 402. In this case, conductive body fluid or tissue fills the shunt gates 500. Alternatively, the carrier 402 can be made with shunt gates 500 formed of an electrically conductive or low impedance (collectively herein referred to as "low-impedance") material, such as electrodeposited platinum columns or a conductive polymer, such as polypyrrole. Optionally, some of the shunt gates 500 are open passages and others are low impedance material in the carrier 402.

The electrical resistance (R) of the shunt gates 500 is calculated according to the equation:

$$R=(R_0 L)/A$$

where $R_0$ is the resistivity of the bodily fluid or tissue in the bores or the resistivity of the low-impedance material in the shunt gates 500; L is the length of each shunt gate 500 (typically, the thickness 412 of the carrier 402); and A is the cross-sectional or surface area of the shunt gates 500. A low resistance (R) can be achieved by using a large area (A) and/or a small length (L).

Figure 7:
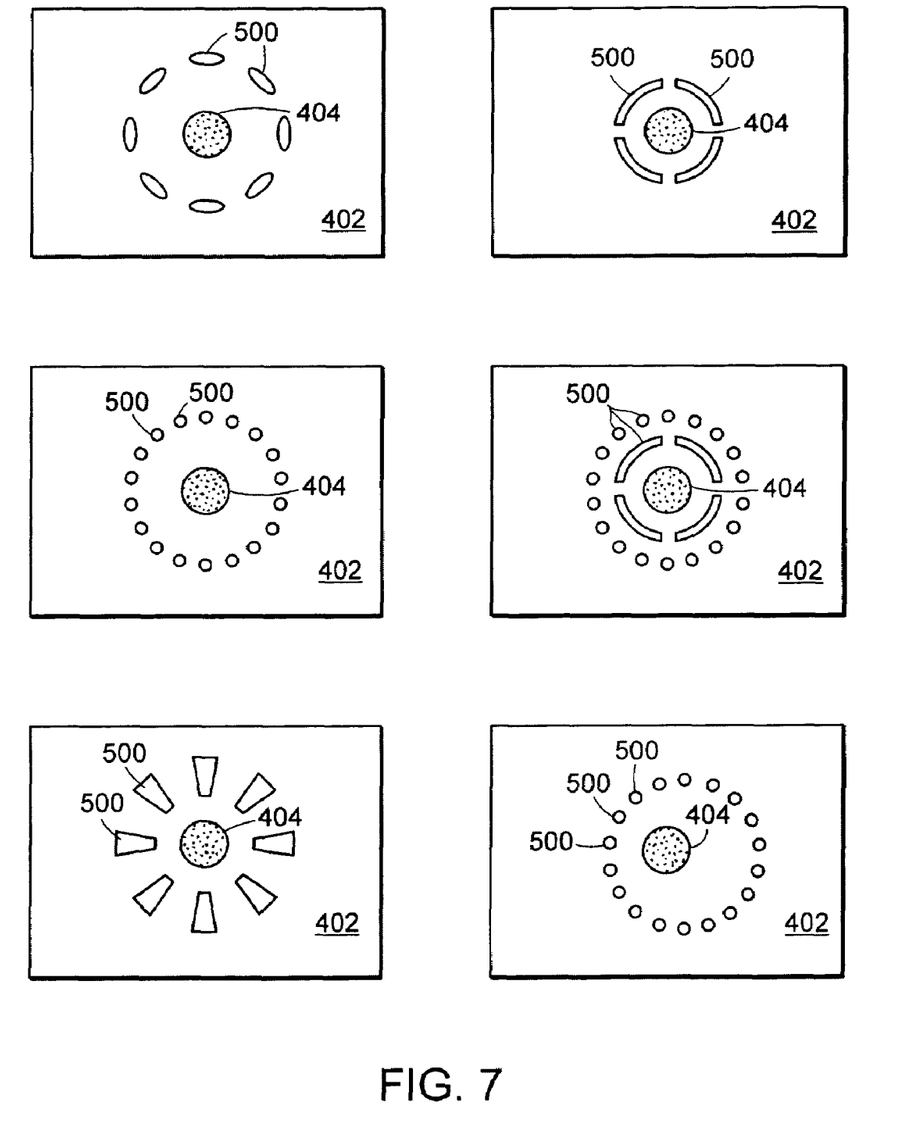
FIG. 7 is a top view of several exemplary shapes and arrangements of shunt gates, according to several embodiments of the present invention.

Although the shunt gates 500 shown in FIG. 6 are straight, narrow slots arranged in a symmetric, rectilinear fashion, other shunt gate shapes, symmetries/asymmetries and arrangements may be used. FIG. 7 illustrates other exemplary, but non-limiting, shapes, symmetries/asymmetries and arrangements.

In addition, the shunt gates need not be perpendicular to the surface of the carrier. For example, as shown in FIG. 5, a shunt gate 502 can be formed at an angle other than 90° to the surface of the carrier 402.

Furthermore, the distances between the shunt gates 500 and the stimulating electrode 404 can be varied. That is, not all the shunt gate 500 need be disposed the same distance from the stimulating electrode 404. The number, shape(s), arrangement, angle(s) and placement(s) (relative to the stimulating electrode 402) of the shunt gates 500 can be selected to shape and orient the stimulation field, as desired. For example, the distance between the stimulating electrode 404 and the shunt gates 500 can be selected to generate a stimulation field having a desired shape and/or orientation. Alternatively or in addition, the shunt gates 500 can be positioned symmetrically or asymmetrically around the stimulating electrode 404. The thickness 412 of the carrier can be selected to achieve a desired path length between the stimulating electrode 404 and the return electrode 406. As long as the path length is relatively low, the stimulation field may be affected by the other geometric parameters described above.

Array of Stimulating Electrodes

The above-described neural stimulator 400 includes one stimulating electrode 404 and one return electrode 406. However, in other embodiments, exemplified by a neural stimulator 800 shown in FIG. 8, several stimulating electrodes 802 are disposed on a single nonconductive carrier 804. For example, for spinal cord stimulation, the neural stimulator 800 may contain hundreds of stimulating electrodes 802 on a carrier that may be about 1 cm by 3 cm. Other numbers of stimulating electrodes 802 and other dimensions may be used.

Figure 8:
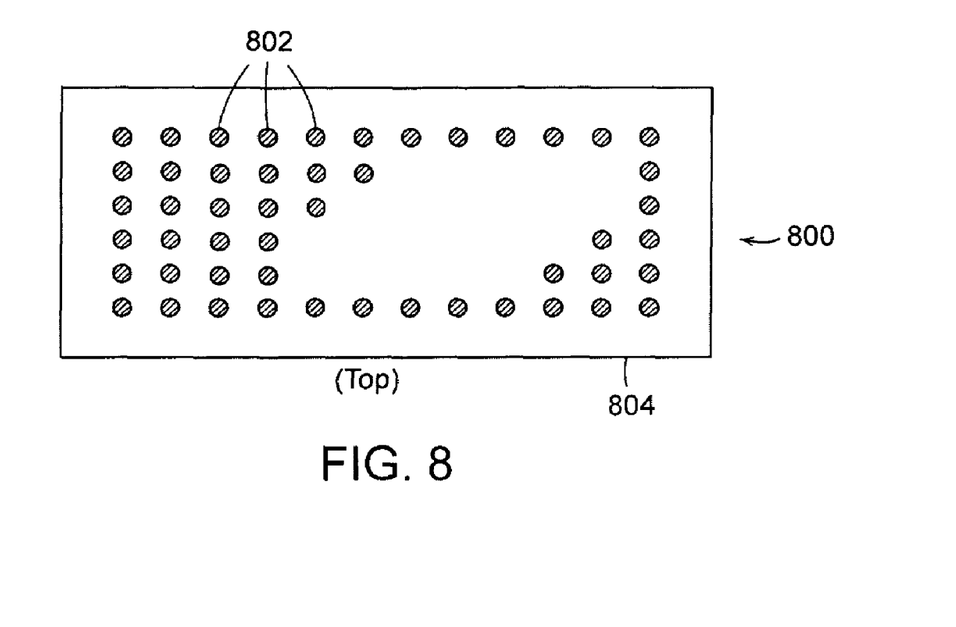
FIG. 8 is a top view of a neural stimulator, according to yet another embodiment of the present invention.

Typically, although not necessarily, each of the electrodes 802 is connected by a separate lead (not shown) to a signal source (not shown). In some embodiments, each electrode 802 has its own signal source. Optionally, a switching matrix or other circuit (not shown) is connected between one or more signal sources and the electrodes 802 to select which electrode(s) 802 is provided with a stimulating signal at a given time and, optionally, which signal source is connected to the electrode(s) 802. Thus, each of the electrodes 802 can be separately supplied with a stimulation signal, or not supplied with any signal. Consequently, as may be the case in a CI, individual areas of neural tissue can be stimulated by individual electrodes 802 or groups of electrodes 802. Optionally, groups of the electrodes 802 can be electrically connected together and, thus, receive a common stimulation signal.

In some embodiments, each of the stimulating electrodes 802 has a corresponding return electrode (not visible in FIG. 8) disposed on the opposite side of the carrier 804. These return electrodes can each have an associated lead in the carrier 804 to provide a return path to the signal source. The return electrodes can, but need not, have the same size and shape as the corresponding stimulating electrodes 802. Alternatively, the return electrodes can be larger or smaller than the corresponding stimulating electrodes 802. Similarly, the return electrodes can have different shapes than the stimulating electrodes 802.

In some embodiments, each return electrode is centered on a line that extends perpendicularly through the center of the corresponding stimulating electrode 802. In other embodiments, the return electrodes are not co-centered with their corresponding stimulating electrodes 802. In yet other embodiments, a switching matrix or other circuit is used to change, from time to time, which return electrode corresponds to a given stimulating electrode 802.

Ring Electrode

Figure 9:
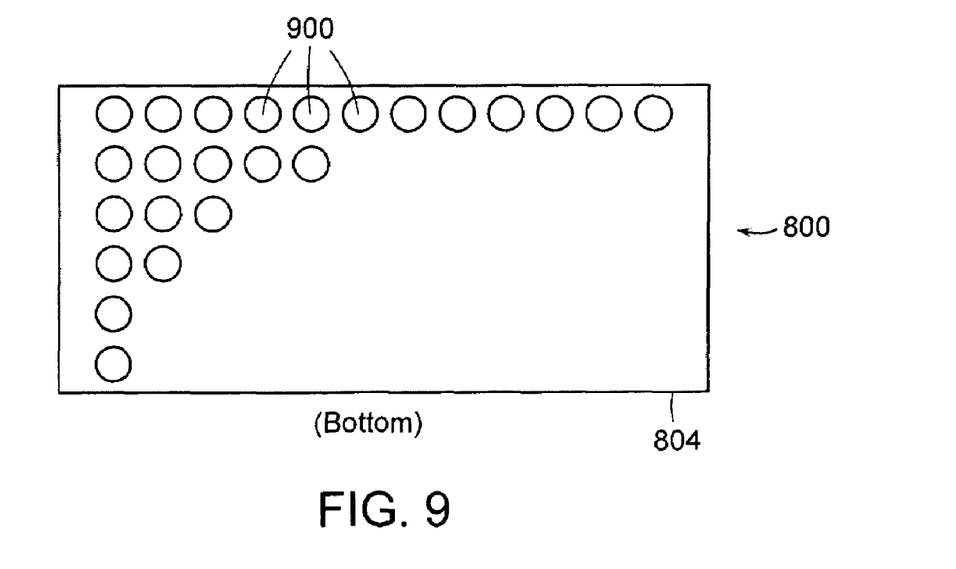
FIG. 9 is a bottom view of the neural stimulator of FIG. 8.

In one embodiment, each return electrode is a conductive ring 900, as shown in FIG. 9. (FIG. 9 is a bottom view of the neural stimulator 800 of FIG. 8.) Alternatively, the return electrodes 900 can be made in other solid or open shapes, such as polygons. Open-shape polygonal return electrodes are referred to herein as "rings," regardless of their shape.

Each return electrode 900 is preferably centered on its corresponding stimulating electrode 802. Alternatively, as discussed above, the return electrodes need not be centered on their corresponding stimulating electrodes. Optionally, as discussed above, a switching matrix or other circuit is used to change, from time to time, which return electrode 900 corresponds to a given stimulating electrode.

Preferably, the total conducting surface area of each ring 900 that is exposed to tissue is approximately equal to the total conducting surface area of the corresponding stimulating electrode 802 that is exposed to tissue. The return electrodes 900 may be fabricated on the carrier 804 using photolithographic, electrodeposition, pulsed laser ablation deposition or other techniques.

Figure 10:
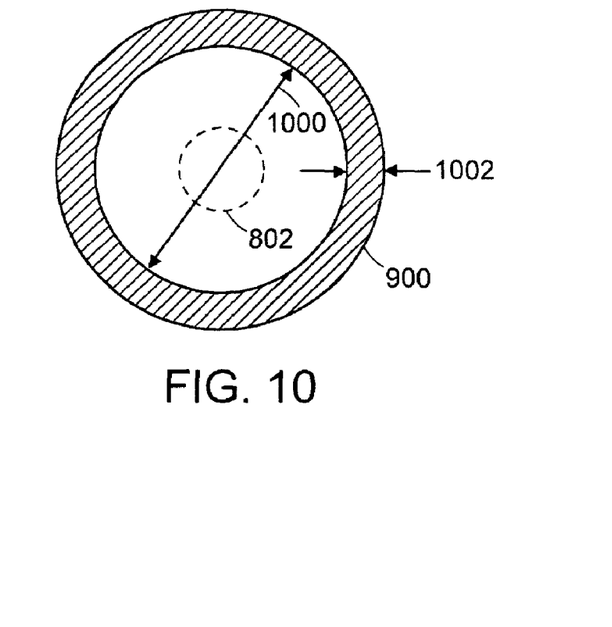
FIG. 10 is a close-up view of a ring electrode, according to one embodiment of the present invention.

In one embodiment, a single ring electrode 900 of which is shown in FIG. 10, each stimulating electrode 802 is about 300µ in diameter, and each ring electrode 900 has an inside diameter 1000 of about 600µ. (In FIG. 10, the stimulating electrode 802 is shown using a dashed line to indicate the stimulating electrode 802 is hidden, i.e., not visible from the bottom of the carrier 804.) The width 1002 of each ring electrode 900 can be calculated, based on the diameter of the stimulating electrode 802 and the diameter 1000 of the ring 900, such that the two electrodes have approximately equal surface areas, as discussed above. In general, the width 1002 of the ring electrode 802 is significantly less than the diameter of the stimulating electrode 802. For example, the diameters of the ring 900 and the stimulating electrode 802 may be related as follows:

$$D_{out} - D_{in} \geq D$$

where $D_{out}$ is the outside diameter of the ring 900; $D_{in}$ is the inside diameter 1000 of the ring 900; and D is the diameter of the stimulating electrode 802.

In other embodiments, other sizes of stimulating electrodes 802 and/or other sizes of ring electrodes 900 can be used. For example, stimulating electrodes smaller than about 300µ in diameter may be used, and ring electrodes 900 having inside diameters 1000 of about 1 or 2 mm can be used.

Alternatively, groups of the return electrodes 900 can be electrically connected together to provide a common ground return electrode for a group of the stimulating electrodes 802. In one embodiment, a single conductive plane is used instead of individual return electrodes 900.

Figure 11:
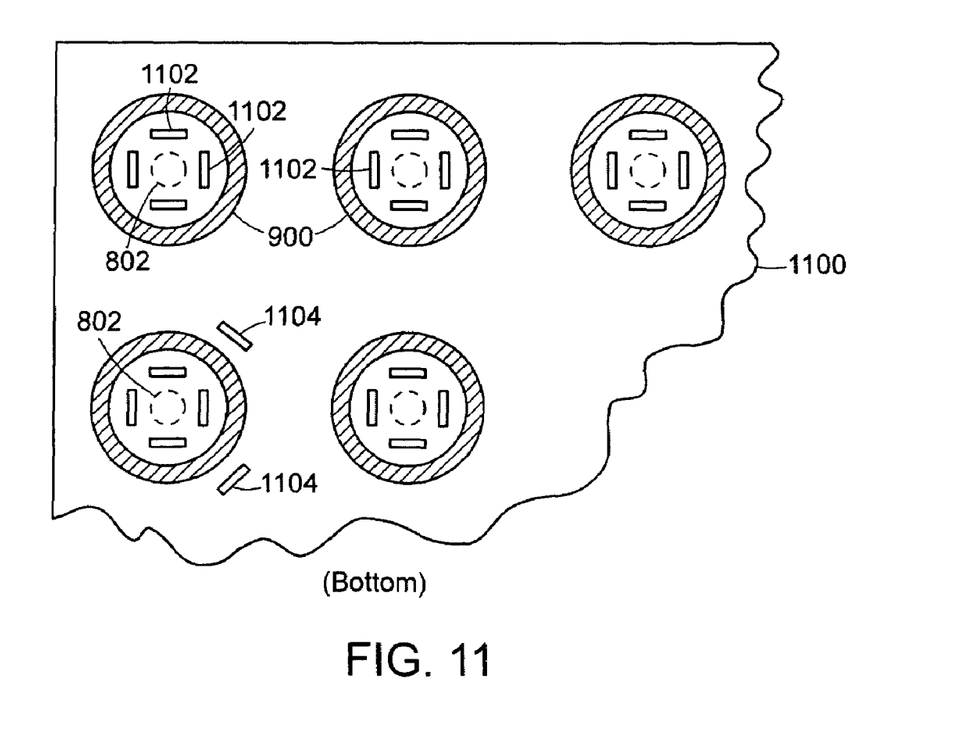
FIG. 11 is a close-up view of a portion of a neural stimulator, according to one embodiment of the present invention.

In yet another embodiment, a portion of which is shown in FIG. 11, a carrier 1100 includes shunt gates 1102 between the ring electrodes 900 and the stimulating electrodes 802. Optionally or alternatively, the carrier 1100 includes shunt gates 1104 outside the ring electrodes 900. As discussed above, the shunt gates 1102 and 1104 can be any shape or size and have any orientation, relative to the stimulating electrodes 802 and the ring electrodes 900. Also, as noted above, some or all the ring electrodes 900 can be electrically connected together. In another embodiment, the bottom of the carrier 1100 is largely covered by a single conductive return electrode, perforated by the shunt gates 1102 and/or 1104.

Electrode Anchors

Figure 12:
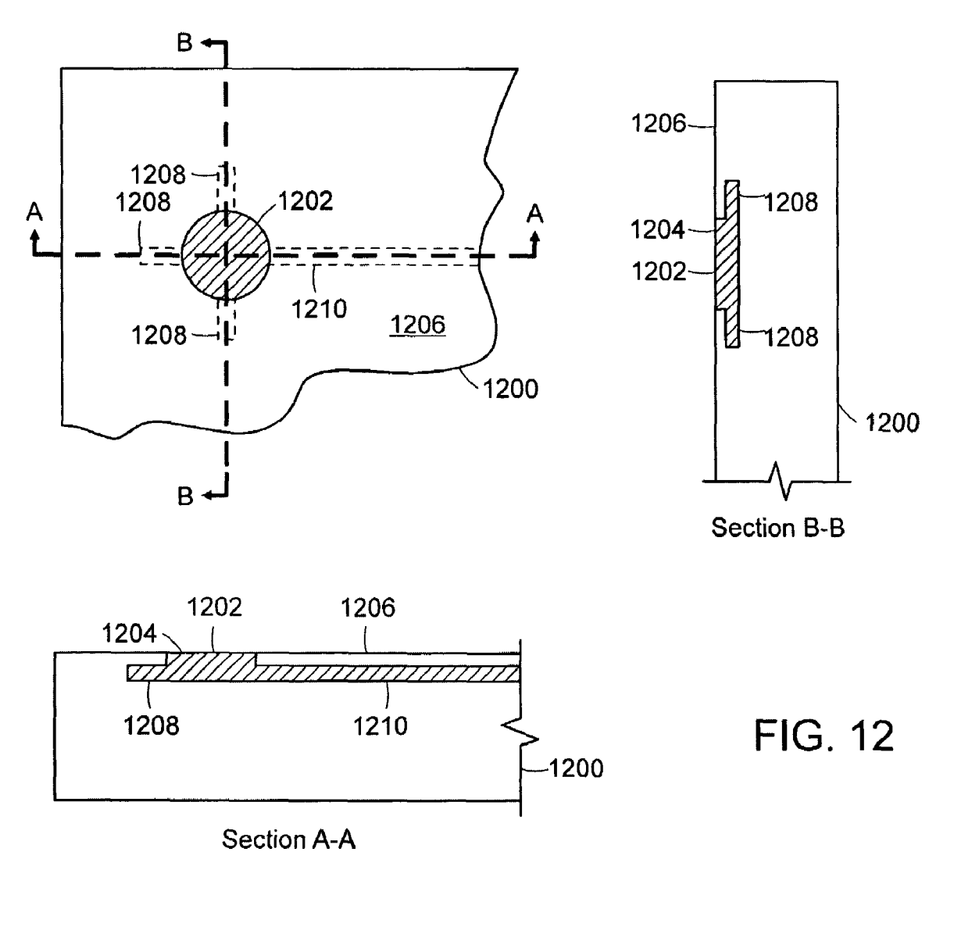
FIG. 12 is a close-up top view and two sectional views of electrode ears, according to one embodiment of the present invention.

As noted, the electrodes are made of conductive material held in a non-conductive carrier. Depending on the materials used and the sizes of the electrodes, some electrodes may include anchors or ears to secure the electrodes to the carrier. As shown in FIG. 12, in one embodiment, a carrier 1200 includes an electrode 1202. Preferably, the surface 1204 of the electrode 1202 is co-planar with the surface 1206 of the carrier 1200, although the surface 1204 of the electrode 1202 can be proud of, or depressed below, the surface 1206 of the carrier 1200. Anchors (ears) 1208 are formed on the electrode 1202 and beneath the surface 1206 of the carrier 1200 to secure the electrode 1202 to the carrier 1200. A lead 1210 connected to the electrode 1202 also secures the electrode 1202 to the carrier 1200. Similar anchors (ears) can be formed on ring (or other shape) electrodes (not shown) to secure the ring electrodes to the carrier 1200.

Stimulation Patterns

Figure 13:
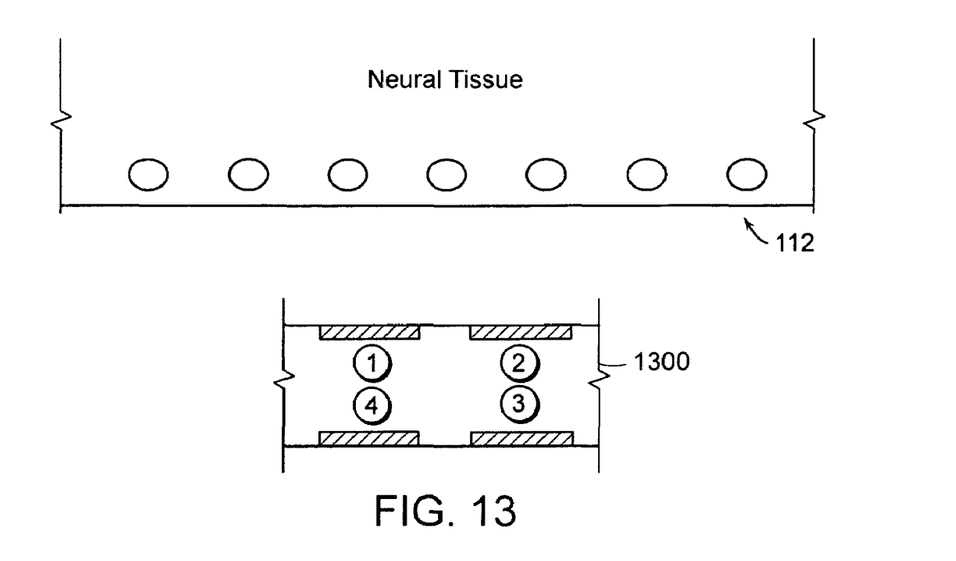
FIG. 13 is a cross-sectional view of a portion of a neural stimulator, according to one embodiment of the present invention.

In an array of one or more stimulating electrodes and one or more return electrodes disposed on opposite sides of a non-conductive carrier, it is possible to generate stimulation fields having various patterns, depending on the number of electrodes and to which pair of stimulating and return electrodes a stimulating signal is sent. For example, as shown in FIG. 13, a carrier 1300 can include four electrodes 1, 2, 3 and 4, any pair of which can be connected to a signal source (not shown). Each of the electrodes 1, 2, 3 and 4 has a lead (not shown), via which the electrode can be connected to the signal source, such as through a switching matrix or other circuit (not shown). Table 1 lists the possible combinations of electrodes that can be connected to the signal source.

TABLE 1

Combinations of Electrodes Connected to a Signal Source

| Electrode(s) | Stimulation Pattern | Comments |
|---|---|---|
| 1 (and a distant ground) | Monopolar | Prior art |
| 2 (and a distant ground) | Monopolar | Prior art |
| 3 (and a distant ground) | Monopolar | Prior art |
| 4 (and a distant ground) | Monopolar | Prior art |
| 1 and 4 | Virtual Radial Quadrupolar | New |
| 2 and 3 | Virtual Radial Quadrupolar | New |
| 1 and 2 | Longitudinal Bipolar | Prior art |
| 3 and 4 | Longitudinal Bipolar | Prior art |
| 1 and 3 | Angled Bipolar | New |
| 2 and 4 | Angled Bipolar | New |

As noted in Table 1, connecting a signal source to one of the electrodes 1, 2, 3 or 4 and to a distant ground electrode is conventional. (The "distant ground" referred to in Table 1 is not shown in the drawings.) Similarly, using two adjacent electrodes on the same side of a carrier, e.g., electrodes 1 and 2 or electrodes 3 and 4, is conventional.

However, as described above, connecting a signal source to two electrodes on opposite sides of the carrier, e.g., electrodes 1 and 4 or electrodes 2 and 3, is novel and provides a better focused stimulation field than in the prior art.

Figure 14:
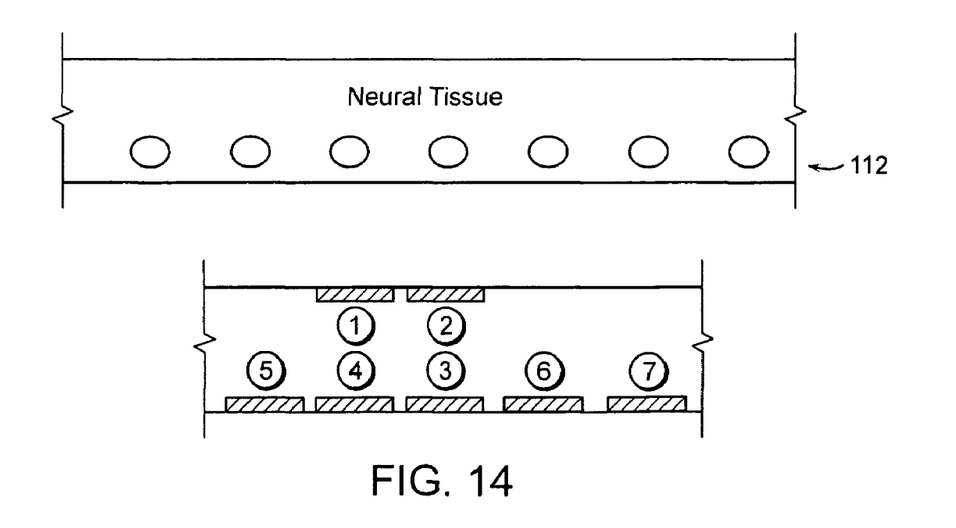
FIG. 14 is a cross-sectional view of a portion of a neural stimulator, according to another embodiment of the present invention.

Furthermore, using a return electrode that is not directly behind a stimulating electrode, e.g., using electrodes 1 and 3 or electrodes 2 and 4, creates a stimulation field that is directed "off-axis," i.e., not along an axis that perpendicularly bisects the stimulating electrode. In this regard, using a carrier that includes more than two return electrodes in the antineural plane, as shown in FIG. 14, and pairing a particular stimulating electrode, such as electrode 2, with one or more of the return electrodes 3-7, the stimulation field can be steered toward selected portions of the neural tissue 112. This steering can provide more spatial resolution than simply selecting a different pair of electrodes that are positioned directly opposite each other on the carrier. Furthermore, the return electrodes 3-7 need not be positioned directly opposite the stimulating electrodes, and the carrier can have more or fewer return electrodes than stimulating electrodes.

Although the neural stimulators shown in FIGS. 13 and 14 include a small number of electrodes, these drawings can alternatively be interpreted to represent only a portion of a neural stimulator that includes many more electrodes (not shown). In addition, the above-described shunt gates can be combined with angled bipolar stimulation. Other combinations of the features described herein are also possible.

While the invention is described through the above-described exemplary embodiments, it will be understood by those of ordinary skill in the art that modifications to, and variations of, the illustrated embodiments may be made without departing from the inventive concepts disclosed herein. Moreover, while some embodiments are described in connection with various illustrative materials and fabrication techniques, one skilled in the art will recognize that the system may be embodied using a variety of other materials or fabrication techniques. Similarly, while some embodiments can be used in cochlear implants (CI), these and other embodiments can be used for other types of neural stimulation, such as cortical, spinal or bladder stimulation, for pain control, diagnosis, neural rehabilitation and other purposes. Accordingly, the invention should not be viewed as limited, except by the scope and spirit of the appended claims.

What is claimed is:

1. A neural stimulator, comprising:
   a nonconductive carrier having a first side and a second side opposite the first side and an interior, wherein the carrier comprises at least two isolated shunt gates, wherein isolated means not in fluid communication with each other via the interior of the carrier, each shunt gate extending entirely through the carrier, from the first side to the second side of the carrier, for providing a low electrical resistance path from the first side to the second side of the carrier;
   at least one first electrically conductive electrode disposed on the first side of the carrier; and
   at least one second electrically conductive electrode disposed on the second side of the carrier, wherein the at least one first electrode is not electrically connected to the at least one second electrode.

2. The neural stimulator defined by claim 1, wherein the carrier has a circular cross-sectional shape.

3. The neural stimulator defined by claim 1, wherein the carrier has an oval cross-sectional shape.

4. The neural stimulator defined by claim 1, wherein the carrier has a rectangular cross-sectional shape.

5. The neural stimulator defined by claim 1, wherein each of the at least one first electrode corresponds to one of the at least one second electrode and each of the at least one second electrode is centered on a line that is perpendicular to, and centered on, the corresponding first electrode.

6. The neural stimulator defined by claim 5, further comprising a signal source connected to one of the at least one first electrode and to the corresponding second electrode.

7. The neural stimulator defined by claim 1, wherein each of the at least one first electrode corresponds to one of the at least one second electrode and each of the at least one second electrode is not centered on a line that is perpendicular to, and centered on, the corresponding first electrode.

8. The neural stimulator defined by claim 7, further comprising a signal source connected to one of the at least one first electrode and to the corresponding second electrode.

9. The neural stimulator defined by claim 1, wherein each shunt gate defines a bore through the carrier.

10. The neural stimulator defined by claim 1, wherein each shunt gate comprises an electrically conductive material.

11. The neural stimulator defined by claim 1, wherein each second electrode comprises a ring electrode, as viewed on the surface of the carrier.

12. The neural stimulator defined by claim 11, wherein each ring electrode is formed by a photolithographic process.

13. The neural stimulator defined by claim 11, wherein each ring electrode is formed by an electrodeposition process.

14. The neural stimulator defined by claim 11, wherein each ring electrode is formed by a laser ablation deposition process.

15. The neural stimulator defined by claim 1, wherein the at least one first electrode comprises a plurality of electrodes arranged in an array.

16. The neural stimulator defined by claim 15, wherein the at least one second electrode comprises a plurality of electrodes, each of the plurality of electrodes comprising a ring electrode, as viewed on the surface of the carrier.

17. The neural stimulator defined by claim 15, wherein the carrier includes at least one shunt gate proximate each first electrode, each shunt gate extending through the carrier, from the first side to the second side of the carrier.

18. The neural stimulator defined by claim 1, wherein each of the at least one first electrode comprises at least one ear disposed below a surface of the carrier.

19. The neural stimulator defined by claim 1, wherein:
   the at least one first electrode comprises a plurality of first electrodes in a region of the first side of the carrier, the region including space between the plurality of first electrodes; and
   the at least one second electrode comprises an electrically conductive surface on the second side of the carrier, the surface having an area at least as large as the region on the first side of the carrier.

20. The neural stimulator defined by claim 1, wherein the at least one second electrode comprises a plurality of electrodes, ones of which are connectable to a signal source.

21. The neural stimulator defined by claim 1, wherein at least one of the shunt gates extends perpendicularly through the carrier.

22. The neural stimulator defined by claim 1, wherein at least one of the shunt gates extends non-perpendicularly through the carrier.

23. The neural stimulator defined by claim 1, wherein each shunt gate comprises a plurality of shunt gates arranged around one of the at least one first electrode.

24. The neural stimulator defined by claim 17, wherein each shunt gate defines a bore through the carrier.

25. The neural stimulator defined by claim 17, wherein each shunt gate comprises an electrically conductive material.

26. A method for stimulating neural tissue, comprising:
   coupling a signal source to a first electrically conductive electrode disposed on a first side of a nonconductive carrier having a second side opposite the first side and an interior, wherein the carrier comprises at least two isolated shunt gates, wherein isolated means not in fluid communication with each other via the interior of the carrier, each shunt gate extending entirely through the carrier, from the first side to the second side of the carrier, for providing a low electrical resistance path from the first side to the second side of the carrier; and
   coupling the signal source to a second electrically conductive electrode located on the second side of the carrier wherein the first electrode is not electrically connected to the second electrode, thereby creating an electrical potential between the first electrode and the second electrode.

27. The method defined by claim 26, wherein coupling the signal source to the second electrode comprises coupling the signal source to an electrode that is centered on a line that is perpendicular to, and centered on, the first electrode.

28. The method defined by claim 26, wherein coupling the signal source to the second electrode comprises coupling the signal source to an electrode that is not centered on a line that is perpendicular to, and centered on, the first electrode.

29. The method defined by claim 26, further comprising creating a stimulation field directed, at least in part, along an axis perpendicular to, and centered on, the first electrode.

30. The method defined by claim 26, further comprising creating a stimulation field directed along an axis not perpendicular to the first electrode.

31. The method defined by claim 26, further comprising steering a stimulation field created by the first electrode and the second electrode.

32. The method defined by claim 26, wherein coupling the signal source to the second electrode comprises coupling the signal source to a plurality of second electrodes located on the second side of the carrier, at least one of the plurality of second electrodes being not centered on a line that is perpendicular to, and centered on, the first electrode.

* * * * *